United States Patent [19]
Orle et al.

[11] Patent Number: 5,508,168
[45] Date of Patent: Apr. 16, 1996

[54] METHODS AND REAGENTS FOR THE DETECTION OF HERPES SIMPLEX VIRUS, TREPONEMA PALLIDUM, AND HAEMOPHILUS DUCREYI

[75] Inventors: Karina A. Orle, San Francisco; Judith B. Weiss, Oakland, both of Calif.

[73] Assignee: Hoffmann-La Roche Inc., Nutley, N.J.

[21] Appl. No.: 243,544

[22] Filed: May 16, 1994

[51] Int. Cl.$^6$ .............................. C12Q 1/70; C12Q 1/68; C12P 19/34; C07H 21/04
[52] U.S. Cl. .................. 435/6; 435/5; 435/91.2; 536/24.3; 536/24.32
[58] Field of Search ................... 435/6, 5, 91.2; 536/23.1, 24.3–24.33

[56] References Cited

U.S. PATENT DOCUMENTS 5,350,842  9/1994  Norgard ................................ 536/23.7

FOREIGN PATENT DOCUMENTS 0452596  10/1991  European Pat. Off. .

OTHER PUBLICATIONS

Parsons et al., 1989, "DNA Probes for the Identification of Haemophilus ducreyi" J. Clinical Microbiology 27(7):1441–1445.
Hay et al., 1990, "Use of the Polymerase Chain Reaction to Detect DNA Sequences Specific to Pathogenic Treponemes in Cerebrospinal Fluid" FEMS Microbiology Letters 68:233–238.
Rossau et al., 1991, "The Development of Specific rRNA-Derived Oligonucleotide Probes for Haemorphilus ducreyi, the Causative Agent of Chancroid" J. General Microbiology 137:277–285.
Burstain et al., Jan., 1991, "Sensitive Detection of Treponema pallidum by Using the Polymerase Chain Reaction" J. Clinical Microbiology 29(1):62–69.
Grimprel et al., Aug., 1991, "Use of Polymerase Chain Reaction and Rabbit Infectivity Testing to Detect Treponema pallidum in Amniotic Fluid, Fetal and Neonatal Sera, and Cerebrospinal Fluid" J. Clinical Microbiology 29(8):1711–1718.
Parsons et al., May, 1991, "Development of a PCR Assay for Haemophilus ducreyi" Abstracts General Meeting American Society Microbiology, Abstract No. D–35.
Wicher et al., Feb., 1992, "Detection of Treponema pallidum in Early Syphillis by DNA Amplification" J. Clinical Microbiology 30(2):497–500.
Weigel et al., Apr., 1992, "Analysis of the N–Terminal Region of the 47–Kilodalton Ingegral Membrane Lipoprotein of Treponema pallidum" Infection and Immunity 60(2):1568–1576.
Parsons et al., Oct., 1992, "Molecular Analysis of the Haemophilus ducreyi groE Heat Shock Operon" Infection and Immunity 60(10):4111–4118.
Chui et al., Mar., 1993, "Development of the Polymerase Chain Reaction for Diagnosis of Chancroid" J. Clinical Microbiology 31(3):659–664.
Persing et al., Diagnostic Molecular Microbiology Principles and Applications, Washington, D.C. American Society for Microbiology, 1993, Chapter 1.7, entitled "PCR Detection of Treponema pallidum".
Parsons et al., May, 1993, "Detection of Haemophilus ducreyi in Genital Ulcer Swabs Using PCR" Abstracts General Meeting American Society Microbiology, Abstract No. D–203.
Johnson et al., Feb., 1994, "Development of a Polymerase Chain Reaction Assay for the Detection of Haemophilus ducreyi" Sexually Transmitted Diseases 21(1):13–23.

*Primary Examiner*—W. Gary Jones
*Assistant Examiner*—Dianne Rees
*Attorney, Agent, or Firm*—George M. Gould; Dennis P. Tramaloni; Douglas A. Petry

[57] ABSTRACT

The present invention provides methods and reagents for the detection and identification of four causative agents of genital ulcerations, herpes simplex virus (HSV) types 1 and 2, *Treponema pallidum*, and *Haemophilus ducreyi*. The methods use sequence-specific primers which enable the simultaneous polymeric chain reaction amplification of genomic nucleic acid sequences from HSV types 1 and 2, *T. pallidum*, and *H. ducreyi*. Following amplification, sequence-specific oligonucleotide probes are used to detect and distinguish HSV type 1 and 2, *T. pallidum*, and *H. ducreyi* nucleic acid.

14 Claims, No Drawings

METHODS AND REAGENTS FOR THE DETECTION OF HERPES SIMPLEX VIRUS, TREPONEMA PALLIDUM, AND HAEMOPHILUS DUCREYI

BACKGROUND OF THE INVENTION

1. Field of the Invention

The present invention relates to the field of molecular biology and nucleic acid chemistry. More specifically, it relates to methods and reagents for detecting and distinguishing herpes simplex virus (HSV) types 1 and 2, *Treponema pallidum*, and *Haemophilus ducreyi*.

2. Description of Related Art

HSV, *T. pallidum*, which is the causative agent of syphilis, and *H. ducreyi*, which is the causative agent of chancroid, are the three primary causative agents of genital ulcerative diseases in the United States. Currently, the diagnosis of genital ulcerative disease is based predominantly on the clinical presentation of the ulcer itself. However, the diagnosis of genital herpes, syphilis, or chancroid is made difficult by the overlapping patterns of clinical presentation and the occurrence of multiple or mixed infections (see Sturm et al., 1987, *Microbiol. Rev.* 63:98–101). Because specific and distinct therapies are required for the treatment of infections with each of these agents, diagnostic tests are needed which accurately identify and distinguish the causative agents of genital ulcers.

HSV normally is detected by viral culture. However, the sensitivity of detection depends on the stage and duration of the lesion. Although the sensitivity of detection by viral culture from vesicular lesions approaches 100%, the sensitivity of detection from crusted or healing lesions drops to 30%.

*T. pallidum* normally is detected by one of two methods. The standard immediate test is by darkfield microscopic examination of lesion material. Alternatively, *T. pallidum* infection is identified by the presence of specific antibodies. Darkfield examination has several disadvantages. Darkfield examination requires specialized equipment and an experienced technician, and only provides a detection sensitivity of less than 75%. Similarly, serological detection is of limited usefulness. Detectable antibodies may not appear for a week after the appearance of a lesion and can persist from a previous infection. Furthermore, the assay may require multiple patient visits.

*H. ducreyi* normally is detected by culture. The assay, which is not widely available, only provides a sensitivity of less than 70%.

The invention of the polymerase chain reaction (PCR), a method for amplifying specific sequences of nucleic acids, makes possible the rapid detection of specific nucleic acid sequences present in a sample in what was previously an undetectably low quantity (see U.S. Pat. Nos. 4,683,195; 4,683,202; and 4,965,188, each of which is incorporated herein by reference). Direct detection of an amplified nucleic acid sequence by hybridization with a sequence-specific oligonucleotide probe makes possible the detection of etiologic agents contained in a sample, thereby enabling rapid and sensitive diagnostic assays.

Current PCR-based assays for HSV, *T. pallidum*, and *H. ducreyi* are designed to detect only a single target. A rapid and sensitive diagnostic test assay capable of detecting and identifying HSV types 1 and 2, *T. pallidum*, and *H. ducreyi* in possibly multiply-infected samples has not be described.

SUMMARY OF INVENTION

The present invention provides methods and reagents for the detection and identification of HSV types 1 and 2, *T. pallidum*, and *H. ducreyi*.

One aspect of invention relates to a process for detecting HSV types 1 and 2, *T. pallidum*, and *H. ducreyi* nucleic acid in a sample, wherein the process comprises using PCR to amplify any target nucleic acid sequences that may be present in the sample, and detecting and identifying amplified nucleic acid by hybridization with sequence-specific oligonucleotide probes. Each probe is fully complementary to a sequence that uniquely identifies the intended target. Hybridization is carried out under conditions such that the probes bind to the nucleic acid to form stable hybrid duplexes only if the hybridizing regions of the probes are fully complementary to the nucleic acid.

Another aspect of the invention relates to oligonucleotide primers and probes that enable the simultaneous amplification and specific detection of HSV types 1 and 2, *T. pallidum*, and *H. ducreyi*.

Another aspect of the invention relates to kits useful for the simultaneous amplification and specific detection of HSV types 1 and 2, *T. pallidum*, and *H. ducreyi*. These kits take a variety of forms and comprise, in one embodiment, a set of three primer pairs for the simultaneous amplification HSV types 1 and 2, *T. pallidum*, and *H. ducreyi*, and a panel of probes sufficient to specifically detect and identify the amplified products from HSV types 1 and 2, *T. pallidum*, and *H. ducreyi*. The kits can also comprise one or more amplification reagents, e.g., primers, polymerase, buffers, and nucleoside triphosphates.

DETAILED DESCRIPTION OF THE INVENTION

To aid in understanding the invention, several terms are defined below.

The terms "nucleic acid" and "oligonucleotide" refer to primers, probes, and oligomer fragments to be detected, and shall be generic to polydeoxyribonucleotides (containing 2-deoxy-D-ribose), to polyribonucleotides (containing D-ribose), and to any other type of polynucleotide which is an N glycoside of a purine or pyrimidine base, or modified purine or pyrimidine base. There is no intended distinction in length between the terms "nucleic acid" and "oligonucleotide", and these terms will be used interchangeably. These terms refer only to the primary structure of the molecule. Thus, these terms include double- and single-stranded DNA, was well as double- and single-stranded RNA.

The exact size of an oligonucleotide depends on many factors and the ultimate function or use of the oligonucleotide. Oligonucleotides can be prepared by any suitable method, including, for example, cloning and restriction of appropriate sequences and direct chemical synthesis by a method such as the phosphotriester method of Narang et al., 1979, *Meth. Enzymol.* 68:90–99; the phosphodiester method of Brown et al., 1979, *Meth. Enzymol.* 68:109–151; the diethylphosphoramidite method of Beaucage et al., 1981, *Tetrahedron Lett.* 22:1859–1862; and the solid support method of U.S. Pat. No. 4,458,066, each incorporated herein by reference. A review of synthesis methods is provided in Goodchild, 1990, *Bioconjugate Chemistry* 1(3): 165–187, incorporated herein by reference.

The term "hybridization" refers to the formation of a duplex structure by two single-stranded nucleic acids due to complementary base pairing. Hybridization can occur between complementary nucleic acid strands or between nucleic acid strands that contain minor regions of mismatch. Conditions under which only fully complementary nucleic acid strands will hybridize are referred to as "stringent hybridization conditions". Two single-stranded nucleic acids that are complementary except for minor regions of mismatch are referred to as "substantially complementary". Stable duplexes of substantially complementary sequences can be achieved under less stringent hybridization conditions. Those skilled in the art of nucleic acid technology can determine duplex stability empirically considering a number of variables including, for example, the length and composition of the oligonucleotides, ionic strength, and incidence and type of mismatched base pairs.

The term "probe" refers to an oligonucleotide which forms a duplex structure with a sequence of a target nucleic acid due to complementary base pairing. The probe will consist of a "hybridizing region", which is a region of the oligonucleotide preferably consisting of 10 to 50 nucleotides, more preferably from 15 to 30 nucleotides, corresponding to a region of the target sequence. "Corresponding" means identical to or complementary to the designated nucleic acid. An oligonucleotide probe optionally can be bound to additional molecules which allow for the detection or immobilization of the probe but do not alter the hybridization characteristics of the probe. One of skill in the art will recognize that, in general, the complement of an oligonucleotide probe is also suitable as a probe.

The terms "sequence-specific oligonucleotide" and "SSO" refer to oligonucleotide probes or primers wherein the hybridizing region is exactly (fully) complementary to the sequence to be detected. The use of stringent hybridization conditions, defined as hybridization conditions under which the oligonucleotide will hybridize only to the exactly complementary target sequence, allows the detection of the specific target sequence. Stringent hybridization conditions are well known in the art (see, e.g., Sambrook et al., 1985, *Molecular Cloning—A Laboratory Manual,* Cold Spring Harbor Laboratory, Cold Spring Harbor, N.Y., incorporated herein by reference). Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the base pairs have dissociated. Typically, stringent conditions will be those in which the salt concentration is at least about 0.2 molar at pH 7 and the temperature is at least about 60° C. Relaxing the stringency of the hybridizing conditions will allow sequence mismatches to be tolerated; the degree of mismatch tolerated can be controlled by suitable adjustment of the hybridization conditions.

A sequence-specific oligonucleotide probe or primer that hybridizes to a nucleotide sequence that is characteristic of a specific species is referred to herein as "species-specific". The hybridization of a sample nucleic acid with a species-specific probe under stringent hybridization conditions can be used to identify the sample nucleic acid as originating from a member of the species.

The term "primer" refers to an oligonucleotide, whether natural or synthetic, capable of acting as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. A primer is preferably a single-stranded oligodeoxyribonucleotide. The appropriate length of a primer depends on the intended use of the primer but typically ranges from 15 to 35 nucleotides. Short primer molecules generally require cooler temperatures to form sufficiently stable hybrid complexes with the template. A primer need not reflect the exact sequence of the template but must be sufficiently complementary to hybridize with a template. Primers can incorporate additional features which allow for the detection or immobilization of the primer but do not alter the basic property of the primer, that of acting as a point of initiation of DNA synthesis.

The term "target region" refers to a region of a nucleic acid which is to be analyzed.

The term "thermostable polymerase enzyme" refers to an enzyme that is relatively stable to heat and catalyzes the polymerization of nucleoside triphosphates to form primer extension products that are complementary to one of the nucleic acid strands of the target sequence. The enzyme initiates synthesis at the 3' end of the primer and proceeds in the direction toward the 5' end of the template until synthesis terminates. A purified thermostable polymerase enzyme is described more fully in U.S. Pat. No. 4,889,818, incorporated herein by reference, and is manufactured by Hoffmann-La Roche and commercially available from Perkin-Elmer, Norwalk, Conn.

The terms "amplification reaction mixture" and "polymerase chain reaction mixture" refer to a combination of reagents that is suitable for carrying out a polymerase chain reaction. The reaction mixture typically consists of oligonucleotide primers, nucleotide triphosphates, and a DNA polymerase in a suitable buffer. Examples of amplification reaction mixtures are provided in the Examples.

Conventional techniques of molecular biology and nucleic acid chemistry, which are within the skill of the art, are fully explained fully in the literature. See, for example, Sambrook et al., 1985, supra; Oligonucleotide Synthesis (M. J. Gait, ed., 1984); *Nucleic Acid Hybridization* (B. D. Hames and S. J. Higgins eds., 1984); and a series, *Methods in Enzymology* (Academic Press, Inc.), all of which are incorporated herein by reference.

The present invention provides methods and reagents for a diagnostic assay capable of detecting and identifying HSV types 1 and 2, *T. pallidum,* and *H. ducreyi.* Primer pairs are provided that function in a single PCR to enable the amplification of target sequences from any or all of the species. Identification of amplified nucleic acid is then carried out by hybridizing the amplified product with sequence-specific oligonucleotide probes and detecting the formation of hybrid duplexes.

To detect HSV types 1 and 2, a region of the gB alkaline exonuclease gene is amplified using primers KS30 (SEQ ID NO: 1) and KS31 (SEQ ID NO: 2). The gB alkaline exonuclease genes from HSV types 1 and 2 are highly homologous to each other, but not to any other known gene sequence in the herpes virus family. The primers hybridize to conserved sequences which are unique to HSV types 1 and 2 and, thereby, enable the specific amplification of both HSV types 1 and 2 using a single pair of primers. Identification of the amplified DNA is carried out by hybridization with sequence-specific probes selected from probe KS38 (SEQ ID NO: 3), which is specific to HSV type 1, probe KS47 (SEQ ID NO: 4), which is specific to HSV type 2, and probe KS54 (SEQ ID NO: 5), which hybridizes to both HSV type 1 and HSV type 2. The probes of the invention provide the options of distinguishing HSV types 1 and 2 or detecting HSV sequences regardless of type. The nucleotide sequences of these primers and probes are listed below, shown in the 5' to 3' direction.

| Primers and Probes for HSV | | |
|---|---|---|
| | Seq ID No. | Sequence |
| Primer | | |
| KS30 | 1 | TTCAAGGCCACCATGTACTACAAAGACGT |
| KS31 | 2 | GCCGTAAAACGGGGACATGTACACAAAGT |
| Probe | | |
| KS38 | 3 | GCCAACGCCGCGACCCGCAC |
| KS47 | 4 | CAAGCCGGCGAAGGTCGCCACG |
| KS54 | 5 | GGTCTCGTGGTCGTCCCGGTGAAA |

To detect *T. pallidum*, a region of the 47 kilodalton membrane immunogen gene is amplified using primers KO3A (SEQ ID NO: 6) and KO4 (SEQ ID NO: 7). The 47 kilodalton immunogen gene is unique to *T. pallidum*, and the gene sequence is invariant among isolates of *T. pallidum*. Consequently, the primers, which are specific to *T. pallidum*, are usable to amplify all strains of *T. pallidum*. Identification of the amplified product is carried out by hybridization with a sequence-specific probe that is either probe KO17 (SEQ ID NO: 8) or probe KO18 (SEQ ID NO: 9). The nucleotide sequences of these primers and probes are listed below, shown in the 5' to 3' direction.

| Primers and Probes for *T. pallidum* | | |
|---|---|---|
| | Seq ID No. | Sequence |
| Primer | | |
| KO3A | 6 | GAAGTTTGTCCCAGTTGCGGTT |
| KO4 | 7 | CAGAGCCATCAGCCCTTTTCA |
| Probe | | |
| KO17 | 8 | CGGGCTCTCCATGCTGCTTACCTTA |
| KO12 | 9 | TCGTGCGGGCTCTCCATGCTGCTTA |

To detect *H. ducreyi*, a region of the 16S small subunit ribosomal RNA (rRNA) gene is amplified using the species-specific primers, KO7A (SEQ ID NO: 10) and KO8A (SEQ ID NO: 11). Detection and identification of the amplified product is carried out by hybridization with the species-specific probe, KO15 (SEQ ID NO: 12). The nucleotide sequences of these primers and probes are listed below, shown in the 5' to 3' direction.

| Primers and Probes for *H. ducreyi* | | |
|---|---|---|
| | Seq ID No. | Sequence |
| Primer | | |
| KO7A | 10 | CAAGTCGAACGGTAGCACGAAG |
| KO8A | 11 | TTCTGTGACTAACGTCAATCAATTTTG |
| Probe | | |
| KO15 | 12 | CCGAAGGTCCCACCCTTTAATCCGA |

The three detection systems described above can be used separately if the detection of a single species is desired. However, a major advantage of the present pairs of amplification primers is that the three pairs of primers can be used simultaneously in the same reaction mixture to amplify nucleic acid from any or all of the four species. The primers have been designed not only to amplify their respective targets under identical conditions, but to avoid cross-hybridization or primer-dimer formation with the other primers. Eliminating the need for separate amplification reactions greatly simplifies the identification of the causative agent of genital ulcerations.

Following amplification with the three pairs of primers, the amplified product is detected and identified by hybridization with the species-specific probes. Because of the occurrence of multiple infections, more than one amplified sequence may be present following amplification. Each of the probes not only specifically detects the sequence amplified using one primer pair, but does not cross-hybridize with the sequences amplified using the other two primer pairs. Additionally, the length and sequence composition of each probe was chosen to allow hybridization under the same conditions. Hence, the probes can conveniently be used in detection assays which require uniform hybridization conditions, such as when used on a single plate in a microwell plate detection assay, or bound to a single membrane in a reverse dot-blot format.

The primers and probes provided above were designed to detect HSV, *T. pallidum* and *H. ducreyi* nucleic acid in clinical samples which may contain nucleic acids from one or more of a variety of infectious organisms. The specificity of the co-amplification and detection assay was assessed empirically, as described in the Examples below. Samples were assayed that contained nucleic acid from a large number of organisms, including commensal and pathogenic microbes that are also found in the genito-urinary tract or in the normal skin flora, and organisms closely related to HSV, *T. pallidum* and *H. ducreyi*. Only nucleic acid sequences from HSV, *T. pallidum* and *H. ducreyi* were amplified using the primer pairs of the invention. The amplification products were detected and correctly identified by hybridization to the sequence-specific probes.

The polymerase chain reaction (PCR) amplification process is well known in the art and described in U.S. Pat. Nos. 4,683,195; 4,683,202; and 4,965,188, each incorporated herein by reference. Commercial vendors, such as Perkin Elmer, Norwalk, Conn., market PCR reagents and publish PCR protocols. For ease of understanding the advantages provided by the present invention, a summary of PCR is provided.

In each cycle of a PCR amplification, a double-stranded target sequence is denatured, primers are annealed to each strand of the denatured target, and the primers are extended by the action of a DNA polymerase. The process is repeated typically between 25 and 40 times. The two primers anneal to opposite ends of the target nucleic acid sequence and in orientations such that the extension product of each primer is a complementary copy of the target sequence and, when separated from its complement, can hybridize to the other primer. Each cycle, if it were 100% efficient, would result in a doubling of the number of target sequences present.

Due to the enormous amplification possible with the PCR process, small levels of DNA carryover from samples with high DNA levels, positive control templates, or from previous amplifications can result in PCR product, even in the absence of purposefully added template DNA. If possible, all reaction mixes are set up in an area separate from PCR product analysis and sample preparation. The use of dedicated or disposable vessels, solutions, and pipettes (preferably positive displacement pipettes) for RNA/DNA preparation, reaction mixing, and sample analysis will minimize cross contamination. See also Higuchi and Kwok, 1989, *Nature*, 339:237–238 and Kwok, and Orrego, in: Innis et al. eds., 1990 *PCR Protocols: A Guide to Methods and Application*, Academic Press, Inc., San Diego, Calif., which are incorporated herein by reference.

Enzymatic methods to reduce the problem of contamination of a PCR by the amplified nucleic acid from previous reactions are described in PCT Patent Publication No. WO 92/01814 and U.S. Pat. No. 5,035,996, both incorporated herein by reference. The methods allow the enzymatic degradation of any amplified DNA from previous reactions. PCR amplifications are carried out in the presence of dUTP instead of dTTP. The resulting double-stranded amplification product which incorporates uracil is subject to degradation by uracil-N-glycosylase (UNG), whereas normal thymine-containing DNA is not degraded by UNG. Amplification reaction mixture are treated with UNG before amplification to degrade all uracil-containing DNA that could serve as target. Because the only source of uracil-containing DNA is the amplified product of a previous reaction, this method effectively eliminates the problem of contamination from previous reactions (carryover). UNG is rendered temporarily inactive by heat, so the denaturation steps in the amplification procedure also serve to inactivate the UNG. New amplification products, therefore, though incorporating uracil, are formed in an UNG-inactivated environment and are not degraded.

Both amplification of target genomic sequences and detection by hybridization with sequence-specific probes are important to obtain sufficient sensitivity and specificity. The sequence-specific oligonucleotide probes of the present invention are designed to be complementary to nucleotide sequences which are known to occur only in the species to be detected. The SSO probes, when used under stringent hybridization conditions wherein probes hybridize only to fully complementary sequences, enable the detection and discrimination of the HSV viruses types 1 and 2, *T. pallidum* and *H. ducreyi*.

The assay methods for detecting hybrids formed between SSO probes and target nucleic acid sequences can require that the probes be bound to additional compounds which facilitate detection or immobilization of the probe. Such additional compounds bound to the probes to allow detection or immobilization should not affect the hybridization properties of the probes which enable the detection and discrimination of HSV types 1 and 2, *T. pallidum* and *H. ducreyi*.

Probes can be bound to a label detectable by spectroscopic, photochemical, biochemical, immunochemical, or chemical means. Useful labels include $^{32}P$, fluorescent dyes, electron-dense reagents, enzymes (as commonly used in ELISAS), biotin, or haptens and proteins for which antisera or monoclonal antibodies are available. Probes also can be bound to additional compounds that are used to immobilize the probe on a solid support.

Labeled probes of the invention can be synthesized and labeled using the techniques described above for synthesizing oligonucleotides. For example, the probe may be labeled at the 5'-end with $^{32}P$ by incubating the probe with $^{32}P$-ATP and kinase. A suitable non-radioactive label for SSO probes is horseradish peroxidase (HRP). Methods for preparing and detecting probes bound to this label are described in the Examples, below, and in U.S. Pat. Nos. 4,914,210, and 4,962,029; both incorporated herein by reference. The use of such labeled probes is also described in U.S. Pat. No. 4,789,630; Saiki et al., 1988, *N. Eng. J. Med.* 319:537–541; and Bugawan et al., 1988, *Bio/Technology* 6:943–947, each of which is incorporated herein by reference. Useful chromogens for the detection of HRP-labeled probes include red leuco dye and 3,3',5,5'-tetramethylbenzidine (TMB).

Examples of additional compounds bound to probes to allow immobilization of the probes include a long poly-dT "tail" that can be fixed to a nylon support by irradiation, a technique described in more detail in PCT Patent Publication No. 89/11548, incorporated herein by reference.

The probes of the invention are used to detect and identify the nucleotide sequences present in a sample by determining which probes hybridize to the nucleic acid sequences present in the sample. Suitable assay methods for detecting hybrids formed between probes and target nucleic acid sequences in a sample are known in the art (Sambrook et al., 1985, supra). Examples include the dot blot and reverse dot blot assay formats.

In a dot blot format, unlabeled amplified target DNA is immobilized on a solid support, such as a nylon membrane. The membrane-target complex is incubated with labeled probe under suitable hybridization conditions, unhybridized probe is removed by washing under suitably stringent conditions, and the membrane is monitored for the presence of bound probe.

An alternate format is a "reverse" dot blot format, in which the amplified target DNA is labeled and the probes are immobilized on a solid support, such as a nylon membrane. The target DNA is typically labeled during amplification by the incorporation of labeled primers. The membrane-probe complex is incubated with the labeled sample under suitable hybridization conditions, unhybridized sample is removed by washing under suitably stringent conditions, and the filter is then monitored for the presence of bound target DNA.

Alternatively, the reverse dot blot assay can be carried out using a solid support having a plurality of probe hybridization sites or wells. In a preferred embodiment of the invention that is particularly useful for large scale clinical applications of the present methods, hybridization is carried out in a microwell plate. A reverse dot blot assay utilizing a microwell plate is described in copending U.S. patent application Ser. No. 695,072, filed May 3, 1991, which is a CIP of U.S. Ser. No. 414,542, filed Nov. 20, 1991, now abandoned, both incorporated herein by reference. Probes can be immobilized to a microwell plate either by passive binding or by first conjugating the probes to bovine serum albumin (BSA), which adheres to microwell plates.

In an alterative method of immobilizing hybridization duplexes for detection, BSA-conjugated species-specific probes are bound to magnetic microparticles. The probes are hybridized in solution to labeled amplification product. Hybridization duplexes are then removed from solution magnetically; the magnetically immobilized hybridization duplexes are then detected as in the methods described above.

Another suitable assay method system is described in U.S. Pat. No. 5,210,015, incorporated herein by reference, in which a labeled probe is added during the PCR amplification process. The probes are modified so as to prevent the probe from acting as a primer for DNA synthesis. Any probe which hybridizes to target DNA during each synthesis step is degraded by the 5' to 3' exonuclease activity of the DNA polymerase, e.g., Taq DNA polymerase. The degradation product from the probe is then detected. Thus, the presence of probe breakdown product indicates that hybridization between probe and target DNA occurred.

One of skill in the art will recognize that the use of different detection assay labels or immobilization methods may require minor optimizations in conditions and/or probe sequences. Whatever the method for determining which SSO probes of the invention hybridize to the target nucleic acid sequences in a sample, the central feature of the typing method involves the identification of the nucleic acid present in the sample by detecting hybridization of oligonucleotide probes to amplified target DNA. The specific application will determine which probes are used. For instance, if the presence or absence of only one of the species is of interest, a single sequence-specific probe is adequate.

The present invention also relates to kits, multicontainer units comprising useful components for practicing the present method. A useful kit can contain a PCR reagent mixture containing the three pairs of primers for amplifying HSV types 1 and 2, *T. pallidum* and *H. ducreyi*. Additionally, a kit can contain a set of probes specific for HSV types 1 and 2, *T. pallidum* and *H. ducreyi* nucleic acid. In some cases, the SSO probes may be fixed to an appropriate support membrane, such as a microwell plate. Other optional components of the kit include, for example, an agent to catalyze the synthesis of primer extension products, the substrate nucleoside triphosphates, means used to label (for example, an avidin-enzyme conjugate and enzyme substrate and chromogen if the label is biotin), the appropriate buffers for PCR or hybridization reactions, and instructions for carrying out the present method.

The examples of the present invention presented below are provided only for illustrative purposes and not to limit the scope of the invention. Numerous embodiments of the invention within the scope of the claims that follow the examples will be apparent to those of ordinary skill in the art from reading the foregoing text and following examples.

EXAMPLE 1

Protocols

Preferred amplification and detection protocols are described below. Amplification is carried out using a single PCR with three pairs of primers present. Detection is carried out in a microwell plate assay format in which the sequence-specific probes are immobilized on the plate and the amplified target is labeled during amplification. Following hybridization with the amplified target, hybrid duplexes are detected using a colorimetric assay.

Sample Preparation

Genital ulcer swabs are preferred clinical samples for the detection of HSV types 1 and 2, *T. pallidum* and *H. ducreyi*, although a wide variety of bodily fluids may be used. Genital ulcers are swabbed and the swabs are placed in a sample transport medium (STM) consisting of 0.4% sodium dodecyl sulfate and 10 mM Tris-HCl, pH 8.0. The swabs are vigorously agitated in the STM for 15 seconds, the liquid is expressed against the side of the tube, and the swabs are removed. Any excess mucus present in the sample should be removed at this time by collecting it on the swab. The collected sample is stable for 24 hours at room temperature. Samples may be stored at 2°–8° C., but should be processed and tested within 10 days of collection. Prior to amplification, the collected sample is mixed with 1 ml specimen diluent (SD) consisting of 20% Tween-20, 0.1% sodium azide, 10 mM Tris-HCl, pH 8.0. The sample is then vortexed for 5–10 seconds and incubated at room temperature for 10 minutes.

Amplification

PCR amplifications are carried out using the three pairs of primers, KS30 (SEQ ID NO: 1) and KS31 (SEQ ID NO: 2), KO3A (SEQ ID NO: 6) and KO4 (SEQ ID NO: and KO7A (SEQ ID NO: 10) and KO8A (SEQ ID NO: 11), which enable the simultaneous amplification of nucleic acid from HSV types 1 and 2, *T. pallidum* and *H. ducreyi*. PCR amplifications are carried out in a total reaction volume of 100 μl consisting of 50 μl of DNA sample added to 50 μl of reaction mixture. The final reaction concentrations are as follows:

25 pmol each primer

200 μM each dATP, dCTP, dGTP, and dUTP 50 mM KCl 10 mM Tris-HCl, pH 8.3

3.0 mM $MgCl_2$ 12.5% Glycerol 2.5 U Taq DNA polymerase*

1 U UNG*

*Developed and manufactured by Hoffmann-La Roche and commercially available from Perkin Elmer, Norwalk, Conn.

Amplification reactions are carried out in a GeneAmp PCR System 9600, marketed by Perkin Elmer, Norwalk, Conn. The thermal cycler is programmed to provide the following thermal profile.

| Step | | Time |
| --- | --- | --- |
| incubate | | 2 minutes, 50° C. |
| | | 5 minutes, 95° C. |
| 35 cycles | denature | 20 seconds, 95° C. |
| | anneal | 20 seconds, 62° C. |
| | extend | 20 seconds, 72° C. |
| hold | | ≧10 minutes, 72° C. |

The initial 2 minutes incubation provides time for the UNG to degrade any contaminating DNA from previous reactions. The final 10 minute hold, which may be extended to several hours, inactivates any residual UNG and insures that all product synthesis has been completed. Longer final incubations (e.g. overnight) result in the degradation of the amplified target.

Gel Electrophoretic Detection

The presence and quantity of amplified product can be assessed using gel electrophoresis. The detection of amplification product by gel electrophoresis is well known in the literature (see, for example, Sambrook et al., 1989, supra). Preferably, an agarose gel (100 ml of 2% NuSieve and 5% SeaChem) and IX TE (0.089M Tris, 0.089M boric acid, 0.0025M disodium EDTA) running buffer are used. Electrophoresis is carried out at 100 volts for approximately 1 hour. Ethidium bromide (0.5 µg/ml) is added after electrophoresis. The gel is destained briefly in water and the ethidium bromide-stained bands of DNA are visualized using UV irradiation.

Microwell Plate Assay

In this detection scheme, the probes are immobilized to a well of a microwell plate and the amplified target DNA is hybridized to the bound probes. The amplification is carried out using biotinylated primers to allow detection of amplified DNA that hybridizes to the bound probes. The primers are biotinylated as described in Levenson and Chang, 1989, in *PCR Protocols: A Guide to Methods and Applications*, (Innis et al., eds., Academic Press. San Diego) pages 92–112, which is incorporated herein by reference. Note that one or both of the primers can be biotinylated.

To immobilize the species-specific probes on the microwell plates, probes conjugated to BSA are allowed to adsorb to the plastic surface of the individual wells of a microwell plate. Preferably, 96 well plates available from Corning (Corning, N.Y.) are used. Probes are immobilized on the microwell plate at a concentration of 25–100 ng/well, preferably 50 ng/well. Alternately, the probes can be immobilized passively on the plastic surface of a microwell plate as follows. One hundred µl of a solution of 1M $CH_3COONH_4$ containing probe at a concentration of 0.025–3 nanogram/µl are added into each well of a microwell plate. The plate is incubated at 37° C. for 10 to 20 hours (overnight) and then rinsed with PBS/EDTA (PBS is 2.68 mM KCl, 137 mM NaCl, 1.47 mM $KH_2PO_4$, and 8.03 mM $Na_2HPO_4$).

Following amplification, 100 µl of denaturation solution (0.4M NaOH; 80 mM EDTA and 0.005% Thymol blue) are added to each PCR tube. A new pipette tip is used for each tube. If detection is not carried out immediately, the PCR tubes should be stored at −20° C. and briefly warmed to 25° C. to 30° C. prior to opening.

The appropriate number of eight well microwell plate strips (minimally 2 strips) are removed and set into the microwell plate frame. One hundred µl of hybridization/ neutralization buffer (2.5M NaSCN, 80 mM $NaH_2PO_4$, 10 mM $NaH_2PO_4$, and 0.125% Tween 20; pH 5.0±0.2) are pipetted into each well of the microwell plate. Using plugged tips with a multi-channel pipetter, 25 µl of the denatured amplification reaction from each PCR tube in the tray is pipetted to the corresponding well position in the microwell plate. The plate is covered with the microwell plate lid and gently tapped on the side 10 to 15 times. Wells in which proper reagent pipeting has been done will turn light yellow in color. No change or only a slight change in blue color indicates that excess amplified product has been added. This will not affect the assay results, however. The addition of excess amplified product will increase positive OD values but negative OD values will not be affected. The plate is incubated for 60 minutes at 37° C. to allow hybridization.

Following incubation the plate is washed five times with a 1X PCR wash buffer. A 10X concentrate of PCR wash buffer contains 9.94 grams per liter of sodium phosphate dibasic, 4.41 grams per liter sodium phosphate (monobasic), 3.722 grams per liter EDTA, 87.66 grams per liter sodium chloride, 13.7 grams per liter of Tween 20, and 10 grams per liter of Pro Clin 300 (Rohm and Haas, Philadelphia, Pa.). The pH of the solution is adjusted with phosphoric acid (pH 6.5–7.1 is preferred). Washing of the plate may be performed manually or with an automated microwell plate washer programmed accordingly.

For manual washing the contents of the plate are emptied and tapped dry. Three hundred µl of wash solution are added to each well in the plate being tested, and the plate is allowed to soak for 15 to 30 seconds. The plate is again emptied and tapped dry. This wash process is repeated four additional times.

For an automated microplate washer, the following procedure is used. The contents of the wells are aspirated. The washer is programmed to add 350 microliters of working wash solution to each well in the plate being tested, soak for 30 seconds, and aspirate. The steps are repeated four additional times. The plate is then tapped dry.

Avidin-HRP conjugate is prepared as follows. A diluent is prepared that contains 0.1 molar 0.25% Emulsit 25 (DKS International, Inc., Tokyo, Japan); 1.0% Kathon CG (Rohm and Haas, Philadelphia, Pa.); 0.1% phenol; 1.0% bovine gamma globulin. The pH of the diluent solution is adjusted to 7.3 with concentrated HCl. To this diluent, 10 nM of conjugated avidin (Vector Labs, Burlingame, Calif.) is added. One hundred µl of avidin-HRP conjugate is added to each well in the plate being tested. The plate is then covered and incubated 15 minutes at 37° C. and again washed as described above.

A working substrate is prepared by mixing 2.0 ml of substrate A (3 mM hydrogen peroxide, 6.5 mM citrate, and 0.1% Kathon CG) and 0.5 ml of Substrate B (4.2 mM 3,3',5,5' tetramethylbenzidine and 40% dimethylformamide) for each multiple of two 8 well microwell plate strips (16 tests). The working substrate is prepared no more than three hours before use and stored away from direct sunlight. One hundred µl of working substrate (substrate A and B mixture) are added to each well of the plate being tested. The plate is then covered and incubated in the dark for 10 minutes at room temperature (20° C. to 25° C.).

One hundred µl of Stop Reagent (5% $H_2SO_4$) is added to each well being tested. The absorbance of each well of 450 nM is read within one hour of adding the Stop Reagent. In general, an absorbance of at least three times the background level, as measured after the PCR amplification of a sample containing no DNA, is considered to be a positive signal.

EXAMPLE 2

Detection Sensitivity

To assess the sensitivity of the detection assay, known amounts of purified target DNA from HSV-2, *T. pallidum*, and *H. ducreyi* were amplified and assayed using microwell plate hybridization assays as described in Example 1.

Amplifications were carried out from samples containing plasmid DNA constructed to contain one of the target sequences. The plasmid DNAs were purified and quantitated to allow a known number of copies to be added to individual reactions. Prior to amplification, plasmids were linearized using a restriction enzyme which cuts the plasmid at a single site. Each amplification was carried out in a reaction mixture containing all three primer pairs, regardless of the target sequence being amplified. Detection sensitivity was assessed both in amplifications wherein each target was present alone and in amplifications wherein all three targets were present in equal concentrations. Amplifications were carried out using linearized plasmids diluted to a concentration of between $10^{-2}$ and $10^7$ copies. Additional amplifications were carried out to determine the assay sensitivity for each target when amplified in the presence of the other two targets each at a concentration of $10^7$ copies per reaction.

In the amplifications in which each target was present alone, each of the target sequences was successfully amplified and detected from an initial concentration of 1–10 copies per reaction. Similarly, in the amplifications in which the same copy number of each of the three target sequences was added to each reaction, amplification and detection of each of the targets was successful from an initial concentration of between 1–10 copies per reaction. In the amplifications in which 10 copies of one target was added to a reaction containing $10^7$ copies of DNA from each of the other two organisms, although the detected signal intensity was lower, amplification and detection of the 10 copy target was successful in each case.

EXAMPLE 3

Specificity

The specificity of the detection assay described in Example 1 was assessed using samples from large number of organisms prepared essentially as described in Example 1. Organisms selected for testing included commensals and pathogenic microbes that can be found in the genito-urinary tract, organisms that comprise the normal skin flora, and organisms that are closely related to the intended target species. Additionally, ten strains of *H. ducreyi*, representing the 10 known 16S rRNA ribotypes, were obtained from the Center for Disease Control and tested to insure that the assay would detect all known ribotypes.

Samples of the yeast and bacteria tested consisted of cell pellets that contained at least $10^6$ cells. For viral amplifications, samples used were viral isolates from cell culture. Samples of the yeast and bacteria tested were pelleted by centrifugation and washed once with 1 ml PBS. The samples were resuspended in 0.5 ml STM, and frozen in 0.1 ml aliquots. For amplification, aliquots were thawed, diluted in 0.1 ml SD, and 50 μl added to the reaction mixture. For all samples, at least $10^4$ copies of the organismal DNA were added to the PCR reaction.

Amplified samples were assayed both by gel electrophoresis and by hybridization using the sequence-specific probes as described above. Results of the assays are shown below. The presence or absence, denoted "+" or "−", of amplification product, as detected by gel electrophoresis, is noted in the column labeled "amplification". Similarly, detection by probe hybridization is noted in the column labeled with the probe designations as used above. Strains representing the 10 ribotypes of *H. ducreyi* are labeled as designated by the Center for Disease Control. Those organisms which the assay was designed to amplify and detect are shown in bold.

|  | Specificity Amplification | K015 | K017 | KS54 |
|---|---|---|---|---|
| BACTERIA/YEAST | | | | |
| *Achromobacter xerosis* | − | − | − | − |
| *Acinetobacter calcoaceticus* | − | − | − | − |
| *Acinetobacter iwolfi* | − | − | − | − |
| *Actinomyces isrealii* | − | − | − | − |
| *Aerococcus viridans* | − | − | − | − |
| *Aeromonas hydrophila* | − | − | − | − |
| *Agrobacterium radiobacter* | − | − | − | − |
| *Alcaligenes dentrificans* | − | − | − | − |
| *Alcaligenes faecalis* | − | − | − | − |
| *Bacillus subtilis* | − | − | − | − |
| *Bacteroides fragilis* | − | − | − | − |
| *Bifidobacterium adolescentis* | − | − | − | − |
| *Borrelia burgdorferi* | − | − | − | − |
| *Branhamela catarrhalis* | − | − | − | − |
| *Brevibacterium linens* | − | − | − | − |
| *Campylobacter fetus* | − | − | − | − |
| *Campylobacter jejuni* | − | − | − | − |
| *Candida albicans* | − | − | − | − |
| *Candida glabrata* | − | − | − | − |
| *Candida guilliermondii* | − | − | − | − |
| *Candida kruisii* | − | − | − | − |
| *Candida parapsilosis* | − | − | − | − |
| *Candida tropicalis* | − | − | − | − |
| *Chlamydia trachomatis* | − | − | − | − |

-continued

| Specificity Amplification | K015 | K017 | KS54 |
|---|---|---|---|
| Chromobacter violaceum | − | − | − | − |
| Citrobacter freundii | − | − | − | − |
| Clostridium innocuum | − | − | − | − |
| Clostridium perfringens | − | − | − | − |
| Corynebacterium genitalium | − | − | − | − |
| Corynebacterium pseudotuberculosis | − | − | − | − |
| Corynebacterium xerosis | − | − | − | − |
| Cryptococcus neoformans | − | − | − | − |
| Deinococcus radiopugnans | − | − | − | − |
| Derxia gummosa | − | − | − | − |
| Edwardsiella tarda | − | − | − | − |
| Eikenella corrodens | − | − | − | − |
| Entercoccus faecalis | − | − | − | − |
| Entercoccus avium | − | − | − | − |
| Enterobacter cloacae | − | − | − | − |
| Enterococcus facium | − | − | − | − |
| Erysipelothrix rhusiopathiae | − | − | − | − |
| F.Escherichia coli | − | − | − | − |
| Flavobacerium meningosepticum | − | − | − | − |
| Gardnerella vaginalis | − | − | − | − |
| Gemmella haemolysans | − | − | − | − |
| Haemophilus aegypticus | − | − | − | − |
| Haemophilus aphrophilus | − | − | − | − |
| Haemophilus ducreyi | | | | |
| ATCC 27721 | + | + | − | − |
| ATCC 27721 | + | + | − | − |
| ATCC 33940 | + | + | − | − |
| ribotypes: | | | | |
| CDC# 174 | + | + | − | − |
| 175 | + | + | − | − |
| 176 | + | + | − | − |
| 178 | + | + | − | − |
| 179 | + | + | − | − |
| 181 | + | + | − | − |
| 182 | + | + | − | − |
| 186 | + | + | − | − |
| 187 | + | + | − | − |
| 189 | + | + | − | − |
| Haemophilus haemoglobinophilus | − | − | − | − |
| Haemophilus haemolyticus | − | − | − | − |
| Haemophilus influenzas | − | − | − | − |
| Haemophilus paracuniculus | − | − | − | − |
| Haemophilus parahaemolyticus | − | − | − | − |
| Haemophilus parainfluenzae | − | − | − | − |
| Haemophilus segnis | − | − | − | − |
| Kingella kingae | − | − | − | − |
| Klebsiella pneumonias | − | − | − | − |
| Lactobacillus casei | − | − | − | − |
| Lactococcus lactis cremoris | − | − | − | − |
| Lactococcus lactis lactis | − | − | − | − |
| Legionella pneumophila | − | − | − | − |
| Micrococcus luteus | − | − | − | − |
| Mycoplasma pneumoniae | − | − | − | − |
| Mycoplasma genitalium | − | − | − | − |
| Mycoplasma hominis | − | − | − | − |
| Neisseria gonorrhoeae | − | − | − | − |
| Neisseria meningitidis | − | − | − | − |
| Pretostreptoccus anaerobicus | − | − | − | − |
| Propionibacterium acnes | − | − | − | − |
| Proteus mirabilis | − | − | − | − |
| Pseudomonas aeruginosa | − | − | − | − |
| Staphylococcus aureus | − | − | − | − |
| Staphylococcus epidermidis | − | − | − | − |
| Streptococcus agalactiae | − | − | − | − |
| Streptococcus mitus | − | − | − | − |
| Streptococcus mutans | − | − | − | − |
| Streptococcus pneumoniae | − | − | − | − |
| Streptococcus pyogenes | − | − | − | − |
| Streptococcus sanguis | − | − | − | − |
| Treponema pallidum | + | − | + | − |
| Ureaplasma urealyticum | − | − | − | − |
| Vibrio parahaemolyticus | − | − | − | − |
| Yersinia enterocolitica | − | − | − | − |
| VIRUSES | | | | |

|                            | Specificity Amplification | K015 | K017 | KS54 |
|----------------------------|---------------------------|------|------|------|
| CMV                        | −                         | −    | −    | −    |
| EBV                        | −                         | −    | −    | −    |
| HHV-VI                     | −                         | −    | −    | −    |
| HPV 16                     | −                         | −    | −    | −    |
| HPV 18                     | −                         | −    | −    | −    |
| HSV I                      | +                         | −    | −    | +    |
| HSV II−                    | +                         | −    | −    | +    |
| VZV                        | −                         | −    | −    | −    |

No non-specific amplifications were observed; only DNA from the intended targets, HSV, *T. pallidum,* and *H. ducreyi,* was amplified. Furthermore, all strains of the intended target organisms were successfully amplified. Detection and identification of the amplified product was successfully carried out by probe hybridization. The co-amplification and hybridization detection assay provides an accurate method of detecting and identifying HSV, *T. pallidum,* and *H. ducreyi* even in samples co-infected with any of a variety of organisms.

---

We claim:

1. A pair of oligonucleotides primers for the amplification of nucleic acid from a region of the *Treponema pallidum* 47 kilodalton membrane immunogen gene, wherein said pair of primers is KO3A (SEQ ID NO: 6) and KO4 (SEQ ID NO: 7).

2. A pair of oligonucleotides primers for the amplification of nucleic acid from a region of the *Haemophilus ducreyi* 16S ribosomal RNA gene, wherein said pair of primers is KO7A (SEQ ID NO: 10) and KO8A (SEQ ID NO: 11).

3. A set of oligonucleotides primers for the co-amplification of nucleic acid from *Treponema pallidum* and *Haemophilus ducreyi*, wherein said set comprises:

(a) a pair of primers for the polymerase chain reaction amplification of a region of the *Treponema pallidum* 47 kilodalton membrane immunogen gene, wherein said pair of primers is KO3A (SEQ ID NO: 6) and KO4 (SEQ ID NO: 7); and (b) a pair of primers for the polymerase chain reaction amplification of a region of the *Haemophilus ducreyi* 16S ribosomal RNA gene, wherein said pair of primers is KO7A (SEQ ID NO: 10) and KO8A (SEQ ID NO: 11).

4. An oligonucleotide probe for the detection and identification of nucleic acid from *Treponema pallidum*, wherein said probe hybridizes under sequence-specific hybridization conditions to a region of the *Treponema pallidum* 47 kilodalton membrane immunogen gene, wherein said probe is selected from the group consisting of KO 17 (SEQ ID NO: 8), KO18 (SEQ ID NO: 9), and the complements thereof.

5. An oligonucleotide probe for the detection and identification of nucleic acid from *Haemophilus ducreyi*, wherein said probe hybridizes under sequence-specific hybridization conditions to a region of the *Haemophilus ducreyi* 16S ribosomal RNA gene, wherein said probe is KO15 (SEQ ID NO: 12) or the complement thereof.

6. A set of oligonucleotides for the amplification, detection, and identification of nucleic acid from *Treponema pallidum*, wherein said set comprises:

(a) a pair of primers for the polymerase chain reaction amplification of a region of the *Treponema pallidum* 47 kilodalton membrane immunogen gene, wherein said pair of primers is KO3A (SEQ ID NO: 6) and KO4 (SEQ ID NO: 7);

(b) an oligonucleotide probe for the detection and identification of nucleic acid from *Treponema pallidum*, wherein said probe hybridizes under sequence-specific hybridization conditions to a region of the *Treponema pallidum* 47 kilodalton membrane immunogen gene, wherein said probe is selected from the group consisting of KO17 (SEQ ID NO: 8), KO18 (SEQ ID NO: 9), and the complements thereof.

7. A set of oligonucleotides for the amplification, detection, and identification of nucleic acid from *Haemophilus ducreyi*, wherein said set comprises:
(a) a pair of primers for the polymerase chain reaction amplification of a region of the *Haemophilus ducreyi* 16S ribosomal RNA gene, wherein said pair of primers is KO7A (SEQ ID NO: 10) and KO8A (SEQ ID NO: 11); and
(b) an oligonucleotide probe for the detection and identification of nucleic acid from *Haemophilus ducreyi*, wherein said probe hybridizes under sequence-specific hybridization conditions to a region of the *Haemophilus ducreyi* 16S ribosomal RNA gene, wherein said probe is KO15 (SEQ ID NO: 12) or the complement thereof.

8. A set of oligonucleotides for the co-amplification, detection, and identification of nucleic acid from *Treponema pallidum* and *Haemophilus ducreyi*, wherein said set comprises:
(a) a pair of primers for the polymerase chain reaction amplification of a region of the *Treponema pallidum* 47 kilodalton membrane immunogen gene, wherein said pair of primers is KO3A (SEQ ID NO: 6) and KO4 (SEQ ID NO: 7);
(b) an oligonucleotides probe for the detection and identification of nucleic acid from *Treponema pallidum*, wherein said probe hybridizes under sequence-specific hybridization conditions to a region of the *Treponema pallidum* 47 kilodalton membrane immunogen gene, wherein said probe KO17 (SEQ ID NO: 8) or KO18 (SEQ ID NO: 9);
(c) a pair of primers for the polymerase chain reaction amplification of a region of the *Haemophilus ducreyi* 16S ribosomal RNA gene, wherein said pair of primers is KO7A (SEQ ID NO: 10) and KO8A (SEQ ID NO: 11); and
(d) an oligonucleotides probe for the detection and identification of nucleic acid from *Haemophilus ducreyi*, wherein said probe hybridizes under sequence-specific hybridization conditions to a region of the *Haemophilus ducreyi* 16S ribosomal RNA gene, wherein said probe is KO15 (SEQ ID NO: 12).

9. A method for detecting and identifying nucleic acid from *Treponema pallidum* contained in a sample, wherein said method comprises:
(a) mixing said sample with a polymerase chain reaction mixture comprising the primers of claim 1;
(b) subjecting said polymerase chain reaction mixture to conditions under which nucleic acid from *Treponema pallidum* is amplified; and
(c) detecting the presence of amplified nucleic acid sequences.

10. The method of claim 9, wherein said step (c) comprises mixing said polymerase chain reaction mixture with an oligonucleotide probe, wherein said probe is selected from the group consisting of KO17 (SEQ ID NO: 8), KO18 (SEQ ID NO: 9), and the complements thereof, under sequence-specific hybridization conditions, and detecting the presence of said probe hybridized to said amplified nucleic acid.

11. A method for detecting and identifying nucleic acid from *Haemophilus ducreyi* contained in a sample, wherein said method comprises:
(a) mixing said sample with a polymerase chain reaction mixture comprising the primers of claim 2;
(b) subjecting said polymerase chain reaction mixture to conditions under which nucleic acid from *Haemophilus ducreyi* is amplified; and
(c) detecting the presence of amplified nucleic acid sequences.

12. The method of claim 11, wherein said step (c) comprises mixing said polymerase chain reaction mixture with an oligonucleotide probe, wherein said probe is KO15 (SEQ ID NO: 12) or the complement thereof, under sequence-specific hybridization conditions, and detecting the presence of said probe hybridized to said amplified nucleic acid.

13. A method for detecting and identifying nucleic acid from *Treponema pallidum* and *Haemophilus ducreyi* contained in a sample, wherein said method comprises:
(a) mixing said sample with a polymerase chain reaction mixture comprising said primers of claim 3;
(b) subjecting said polymerase chain reaction mixture to conditions under which nucleic acid from *Treponema pallidum* and *Haemophilus ducreyi* is amplified; and
(c) detecting the presence of amplified nucleic acid sequences.

14. The method of claim 13, wherein said step (c) comprises mixing a fraction of said polymerase chain reaction mixture with an oligonucleotide probe, wherein said probe is selected from the group consisting of KO17 (SEQ ID NO: 8), KO18 (SEQ ID NO: 9), and the complements thereof, under sequence-specific hybridization conditions, and detecting the presence of said probe hybridized to said amplified nucleic acid, and separately mixing a fraction of said polymerase chain reaction mixture with a second oligonucleotide probe, wherein said second probe is KO15 (SEQ ID NO: 12) of the complement thereof, under sequence-specific hybridization conditions, and detecting the presence of said probe hybridized to said amplified nucleic acid.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

TTCAAGGCCA CCATGTACTA CAAAGACGT                                              29

( 2 ) INFORMATION FOR SEQ ID NO:2:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GCCGTAAAAC GGGGACATGT ACACAAAGT                                              29

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GCCAACGCCG CGACCCGCAC                                                        20

( 2 ) INFORMATION FOR SEQ ID NO:4:

( i ) SEQUENCE CHARACTERISTICS:
        ( A ) LENGTH: 22 base pairs
        ( B ) TYPE: nucleic acid ( C ) STRANDEDNESS: single
( D ) TOPOLOGY: linear ( i i ) MOLECULE TYPE: DNA (genomic)

( x i ) SEQUENCE DESCRIPTION: SEQ ID NO:4:

CAAGCCGGCG AAGGTCGCCA CG  22

( 2 ) INFORMATION FOR SEQ ID NO:5:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

GGTCTCGTGG TCGTCCCGGT GAAA  24

( 2 ) INFORMATION FOR SEQ ID NO:6:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

GAAGTTTGTC CCAGTTGCGG TT  22

( 2 ) INFORMATION FOR SEQ ID NO:7:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

CAGAGCCATC AGCCCTTTTC A  21

( 2 ) INFORMATION FOR SEQ ID NO:8:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

CGGGCTCTCC ATGCTGCTTA CCTTA  25

( 2 ) INFORMATION FOR SEQ ID NO:9:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

TCGTGCGGGC TCTCCATGCT GCTTA 25

( 2 ) INFORMATION FOR SEQ ID NO:10:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

CAAGTCGAAC GGTAGCACGA AG 22

( 2 ) INFORMATION FOR SEQ ID NO:11:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

TTCTGTGACT AACGTCAATC AATTTTG 27

( 2 ) INFORMATION FOR SEQ ID NO:12:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

CCGAAGGTCC CACCCTTTAA TCCGA 25